12) United States Patent
Adak et al.

(10) Patent No.: US 12,162,957 B2
(45) Date of Patent: Dec. 10, 2024

(54) PROCESS FOR THE PREPARATION OF PLECANATIDE

(71) Applicant: ENZENE BIOSCIENCES LIMITED, Pune Maharashtra (IN)

(72) Inventors: Sandip Adak, Pune Maharashtra (IN); Manoj Bonte, Pune Maharashtra (IN); Chandrakant Kulkarni, Pune Maharashtra (IN); Veeranarayana Swamy, Pune Maharashtra (IN); Nivrutti Jogdand, Pune Maharashtra (IN); Himanshu Gadgil, Pune Maharashtra (IN)

(73) Assignee: ENZENE BIOSCIENCES LIMITED, Pune Maharashtra (IN)

( * ) Notice: Subject to any disclaimer, the term of this patent is extended or adjusted under 35 U.S.C. 154(b) by 266 days.

(21) Appl. No.: 17/311,789

(22) PCT Filed: Apr. 1, 2019

(86) PCT No.: PCT/IB2019/052664
§ 371 (c)(1),
(2) Date: Jun. 8, 2021

(87) PCT Pub. No.: WO2020/115566
PCT Pub. Date: Jun. 11, 2020

(65) Prior Publication Data
US 2022/0033440 A1 Feb. 3, 2022

(30) Foreign Application Priority Data
Dec. 8, 2018 (IN) .............................. 201821046514

(51) Int. Cl.
| C07K 1/04 | (2006.01) |
| C07K 1/00 | (2006.01) |
| C07K 1/06 | (2006.01) |
| C07K 1/107 | (2006.01) |
| C07K 1/36 | (2006.01) |
| C07K 7/08 | (2006.01) |

(52) U.S. Cl.
CPC ............. *C07K 7/08* (2013.01); *C07K 1/003* (2013.01); *C07K 1/047* (2013.01); *C07K 1/061* (2013.01); *C07K 1/1075* (2013.01); *C07K 1/36* (2013.01)

(58) Field of Classification Search
CPC ..... C07K 7/08; C07K 1/04; C07K 1/36; C07K 1/00; C07K 1/06; C07K 1/107
See application file for complete search history.

(56) References Cited

U.S. PATENT DOCUMENTS 9,580,471 B2 * 2/2017 Bai ........................ C07K 7/64
2007/0292322 A1 * 12/2007 Soung ................. B01J 19/0046
422/600

FOREIGN PATENT DOCUMENTS

| CN | 103694320 A | | 4/2014 | |
| CN | 104211777 A | * | 12/2014 | |
| CN | 104628827 A | * | 5/2015 | |
| CN | 107383170 A | * | 11/2017 | ............... C07K 7/08 |
| CN | 104628827 B | | 1/2018 | |
| WO | 2012/18972 A2 | | 2/2012 | |
| WO | 2014/197720 A2 | | 12/2014 | |

OTHER PUBLICATIONS

Benz, The Role of Solid-Phase Fragment Condensation (SPFC) in Peptide Synthesis, Synthesis 1994; 1994(4): 337-358. DOI: 10.1055/s-1994-25472 (Year: 1994).*
Protocols for the Fmoc SPPS of Cysteine-containing Peptides, https://www.sigmaaldrich.com/US/en/technical-documents/protocol/chemistry-and-synthesis/peptide-synthesis/fmoc-spps-cysteine-peptides. (Year: 2018).*
CEM—https://cem.com/peptide-cleavage-and-protected-cleavage-appnote#:~:text=Introduction,and%20removes%20the%20protecting%20groups. (Year: 2017).*
International Search Report and Written Opinion of the International Searching Authority issued on Jul. 23, 2019 in corresponding International application No. PCT/IB2019/052664; 9 pages.

* cited by examiner

*Primary Examiner* — Lianko G Garyu
*Assistant Examiner* — John Cronin
(74) *Attorney, Agent, or Firm* — Maier & Maier, PLLC

(57) ABSTRACT

A process for the preparation of plecanatide. Specifically, an improved process for preparation of plecanatide using a non-linear solid phase peptide synthesis. In particular, the process for preparation of plecanatide involves solid phase synthesis of peptide fragments of five amino acid units using 2-chlorotrityl chloride (2-ClTrt) resin and eleven amino acid unit using Wang resin.

9 Claims, 1 Drawing Sheet
Specification includes a Sequence Listing.

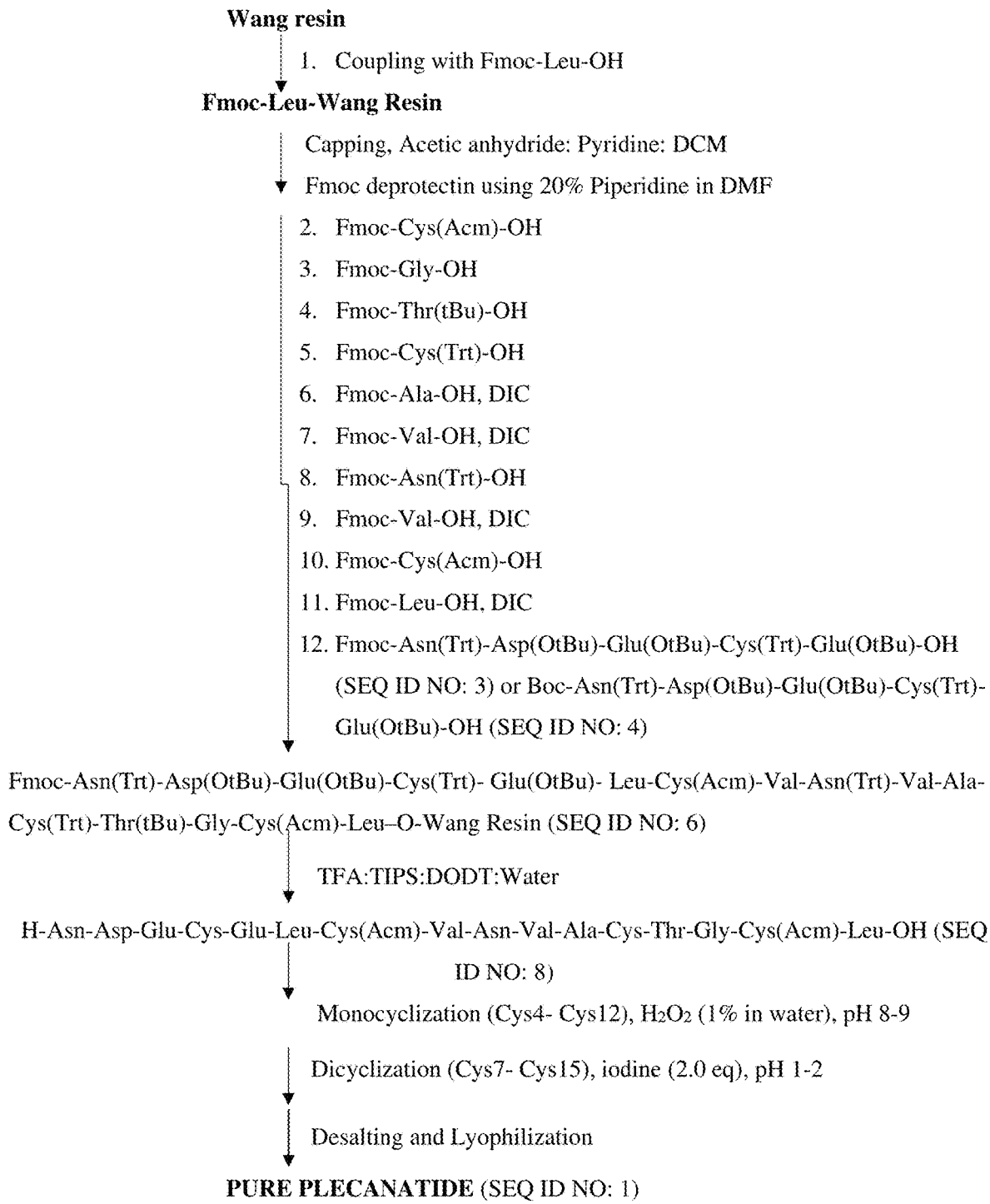

PROCESS FOR THE PREPARATION OF PLECANATIDE

The Sequence Listing associated with this application is filed in electronic format via 10 EFS-Web and is hereby incorporated by reference into the specification in its entirety. The name of the text file containing the Sequence Listing is file "17311789 Sequence Listing ST25.txt.".

FIELD

The present invention relates to an improved process for preparation of plecanatide using a novel non-linear solid phase peptide synthesis. In particular, the process for preparation of plecanatide of the present invention involves solid phase synthesis of fragments of five amino acid units and eleven amino acid unit using Wang resin and 2-chlorotrityl chloride (2-ClTrt) resin.

BACKGROUND

Background description includes information that may be useful in understanding the present invention. It is not an admission that any of the information provided herein is prior art or relevant to the presently claimed invention, or that any publication specifically or implicitly referenced is prior art.

Plecanatide is a drug approved by the FDA for the treatment of chronic idiopathic constipation (CIC) and irritable bowel syndrome with constipation. Plecanatide increases intestinal transit and fluid through a buildup of cGMP.

Plecanatide is a 16 residue peptide which is an agonist of the guanylate cyclase-C peptide with the amino acid sequence, H-Asn1-Asp2-Glu3-Cys4-Glu5-Leu6-Cys7-Val8-Asn9-Val10-Ala11-Cys12-Thr13-Gly14-Cys15-Leu16-OH (SEQ ID NO:1). It is structurally identical to human uroguanylin, apart from the substitution of Asp3 with Glu3. Disulphide bonds exist between Cys4 and Cys12, as well as Cys7 and Cys15.

PCT publication, WO2014197720 discloses the process of purifying or isolating peptides, via a hybrid solution- and solid-phase process, as described in WO2012/18972. In particular, WO2014197720 discloses synthesis of three peptide fragments, A, B and C and then a linear peptide sequence is assembled by the condensation of fragment A, B and C as follows: preparing fragment A, Boc-Asn(Trt)-Asp(OtBu)-Glu(OtBu)-Cys(Trt)-Glu(OtBu)-Leu-OH (i.e. amino acid residues 1-6 SEQ ID NO: 1 of PCT application '720), by solid phase from 2-Chlorotrityl chloride resin; preparing fragment B, Fmoc-Cys(Acm)-Val-Asn-Val-Ala-Cys(Trt)-Thr(tBu)-Gly-OH (i.e. amino acid residues 7-14 of SEQ ID NO: 1 of PCT application '720), by solid phase from 2-chlorotrityl chloride resin; preparing fragment C, Cys(Acm)-Leu-OtBu, by solution phase synthesis, coupling fragments B and C in solution phase to yield fragment B-C, and coupling fragments A and B-C to yield linear peptide A-B-C. The partially protected linear plecanatide (HAA1-16OH) was oxidized by $H_2O_2$, followed by simultaneous removal of the S-Acm groups and disulfide formation with iodine to give crude Plecanatide which was purified through RP-HPLC chromatography to get purified plecanatide.

Chinese Patent publication, CN103694320A discloses preparation of polypeptide drugs and particularly relates to a preparation method of plecanatide. The method comprises the following steps: carrying out solid-phase synthesis to obtain Fmoc-Leu-resin; coupling -Cys15, -Gly, -Thr, -Cys12, -Ala, -Val, -Asn, -Val, -Cys7, -Leu, -Glu, -Cys4, -Glu, -Asp and -Asn on Fmoc-Leu-resin in sequence according to a peptide sequence of the plecanatide to prepare plecanatide linear peptide resin, and cracking to prepare plecanatide linear crude peptide; taking the plecanatide linear crude peptide and carrying out first cyclizing and second cyclizing to obtain the plecanatide.

Although, various processes for preparation of plecanatide are available, the coupling efficiency of the amino acids from Val8 in linear sequence decreases as the chain length increases. Hence, the coupling of Cys7, Leu6, Glu5, Cys4, Glu3, Asp2 and Asn1 remains incomplete tending to formation of related deletion impurities. The generated impurities being less in only one amino acid in the sequence, give rise to close eluting peaks during the purification. This leads to multiple purification cycles lowering the isolated yields of the final product. The impurity profile of the final isolated product also has to be accessed for the presence of the above mentioned impurities.

Therefore, there is a need to develop an improved process which is a simple, efficient and cost-effective process and provides the desired compounds in improved yield and purity.

An object of the present invention is to provide an improved process of preparing plecanatide which is a simple, efficient and cost-effective process.

Another object of the present invention is to provide an improved process of preparing plecanatide which provides the desired compound in improved yield and purity.

Another object of the present invention is to provide an improved process of preparing plecanatide which is commercially scalable for large scale operations.

SUMMARY

The present invention relates to a process for preparation of poly peptide drugs and in particular preparation of plecanatide. Specifically, the present invention relates to a process for preparation of plecanatide which involves solid phase synthesis of fragments of five amino acid unit and eleven amino acid unit using Wang resin and 2-chlorotrityl chloride (2-ClTrt) resin.

In one aspect, the present invention relates to a process for preparing plecanatide comprising the steps of:

(a) monocylizing a linear chain of formula (I), $H_2N$-Asn1-Asp2-Glu3-Cys4-Glu5-Leu6-Cys(Acm)7-Val8-Asn9-Val10-Ala11-Cys12-Thr13-Glyl4-Cys(Acm)15-Leu16-OH (SEQ ID NO:8) with a suitable reagent to obtain a monocyclic peptide of formula (VI) (SEQ ID NO:9), Asn-Asp-Glu-Cys-Glu-Leu-Cys(Acm)-Val-Asn-Val-Ala-Cys-Thr-Gly-Cys(Acm)-Leu-OH, (b) purifying the monocyclic peptide of formula (VI) (SEQ ID NO:9) obtained in step (a) using reverse phase column chromatography, (c) dicyclizing the monocyclic peptide of formula (VI) (SEQ ID NO:9) obtained in step (b) with suitable reagents to obtain dicyclized peptide of formula (VII) (SEQ ID NO: 1),

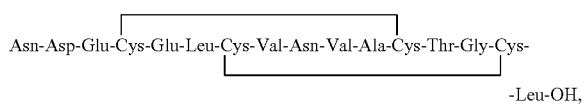

-Leu-OH, and (d) purifying and desalting the dicyclic peptide of formula (VII) (SEQ ID NO:1) obtained in step (c) using reverse phase column chromatography to obtain pure plecanatide.

In another aspect, the present invention relates to the process for preparing plecanatide, wherein the linear chain of formula (I) (SEQ ID NO:8) is obtained by a process comprising the steps of:

(a) coupling fragment A (SEQ ID NO:3) with Wang resin bound fragment B (SEQ ID NO: 5) to obtain a Wang resin bound protected peptide fragment (SEQ ID NO:6);

(b) cleaving and deprotecting the Wang resin bound protected peptide fragment (SEQ ID NO: 6) obtained in step (a) using reagents, trifluoroacetic acid/triisopropylsilane/3,6-dioxa-1,8-octanedithiol (DODT)/Water to obtain the linear chain of formula (I), $H_2N$-Asn1-Asp2-Glu3-Cys4-Glu5-Leu6-Cys(Acm)7-Val8-Asn9-Val10-Ala11-Cys12-Thr13-Gly14-Cys(Acm)15-Leu16-OH (SEQ ID NO:8).

In another aspect, the present invention relates to the process for preparing plecanatide, wherein the reverse phase column chromatography for purifying monocyclic peptide has column specification: 250×80 mm, media specification: C-18, 10μ, 100 A°, mobile phase A: 0.02M triethyl ammonium phosphate in water of pH 6.5 and mobile phase B: acetonitrile.

In another aspect, the present invention relates to the process for preparing plecanatide, wherein the reverse phase column chromatography for purifying the dicyclic peptide of formula (VII) has column specification: 250×80 mm, media specification: C-18, 10μ, 100 A°, mobile phase A: 0.02 M triethyl ammonium phosphate in water of pH 6.5 and mobile phase B: acetonitrile.

In another aspect, the present invention relates to the process for preparing plecanatide, wherein the reverse phase column chromatography for purifying the dicyclic peptide of formula (VII) has column specification: 250×80 mm, media specification: C-18, 10μ, 100 A°, mobile phase A: 0.1-0.2% TFA in water and mobile phase B: acetonitrile.

In another aspect, the present invention relates to the process for preparing plecanatide, wherein the reverse phase column chromatography for desalting the dicyclic peptide of formula (VII) has column specification: 250×80 mm, media specification: C-18, 10μ, 100 A°, mobile phase A: 0.025% ammonium hydroxide, mobile phase B: acetonitrile, mobile phase C: 0.1-0.25M ammonium acetate in water, mobile phase D: 0.1% TFA in water.

In another aspect, the present invention relates to the process for preparing plecanatide, wherein the suitable reagent in monocylizing step is selected from 1% $H_2O_2$ solution.

In another aspect, the present invention relates to the process for preparing plecanatide, wherein the suitable reagent in dicyclizing step is selected from 2% iodine solution.

In another aspect, the present invention relates to the process for preparing plecanatide, wherein the fragment A is Fmoc-Asn(Trt)-Asp(OtBu)-Glu(OtBu)-Cys(Trt)-Glu(OtBu)-OH (SEQ ID NO:3) or Boc-Asn(Trt)-Asp(OtBu)-Glu(OtBu)-[[Cus]]Cys(Trt)-Glu(OtBu)-OH (SEQ ID NO: 4).

In another aspect, the present invention relates to the process for preparing plecanatide, wherein the Wang resin bound fragment B is $H_2N$-Leu-Cys(Acm)-Val-Asn(Trt)-Val-Ala-Cys(Trt)-Thr(OtBu)-Gly-Cys(Acm)-Leu-O-Wang resin (SEQ ID NO: 5).

In another aspect, the present invention relates to the process for preparing plecanatide, wherein the fragment A is not more than 5 amino acid units in length.

In another aspect, the present invention relates to the process for preparing plecanatide, wherein the Wang resin bound fragment B is not more than 11 amino acid units in length.

In another aspect, the present invention relates to the process for preparing plecanatide, wherein the fragment A and fragment B are prepared using solid-phase peptide synthesis.

In another aspect, the present invention relates to the process for preparing plecanatide, wherein the trifluoroacetic acid/triisopropylsilane/DODT/water is in the ratio of 9:0.5:0.25:0.25 v/v respectively.

Various objects, features, aspects and advantages of the inventive subject matter will become more apparent from the following detailed description of preferred embodiments.

BRIEF DESCRIPTION OF THE DRAWINGS

FIG. 1 illustrates the schematic description of the general strategy for process of preparation of plecanatide

DETAILED DESCRIPTION OF THE INVENTION

The following is a detailed description of embodiments of the disclosure. The embodiments are in such detail as to clearly communicate the disclosure. However, the amount of detail offered is not intended to limit the anticipated variations of embodiments; on the contrary, the intention is to cover all modifications, equivalents, and alternatives falling within the spirit and scope of the present disclosure as defined by the appended claims.

All publications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

Unless the context requires otherwise, throughout the specification which follow, the word "comprise" and variations thereof, such as, "comprises" and "comprising" are to be construed in an open, inclusive sense that is as "including, but not limited to."

The recitation of ranges of values herein is merely intended to serve as a shorthand method of referring individually to each separate value falling within the range. Unless otherwise indicated herein, each individual value is incorporated into the specification as if it were individually recited herein.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written The description that follows, and the embodiments described herein, is provided by way of illustration of an example, or examples, of particular embodiments of the principles and aspects of the present disclosure. These examples are provided for the purposes of explanation, and not of limitation, of those principles and of the disclosure.

It should also be appreciated that the present disclosure can be implemented in numerous ways, including as a system, a method or a device. In this specification, these implementations, or any other form that the invention may take, may be referred to as processes. In general, the order of the steps of the disclosed processes may be altered within the scope of the invention.

The headings and abstract of the invention provided herein are for convenience only and do not interpret the scope or meaning of the embodiments.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

Various terms as used herein are shown below. To the extent a term used in a claim is not defined below, it should be given the broadest definition persons in the pertinent art have given that term as reflected in printed publications and issued patents at the time of filing.

The term, "Wang resin" as used herein refers to a polyethylene-based resin, preferably containing p-alkoxybenzyl alcohol or p-alkoxybenzyloxycarbonyl hydrazide based resins. Wang resins are typically removed under strong acid conditions, e.g. at least 50% trifluoroacetic acid solutions. Example of Wang resin includes but not limited to H-Leu-Wang resin or the free resins.

The term, "peptide" as used herein refers to a compound containing at least two amino acids in which the carboxyl group of one amino acid is linked to the amino group of the other (i.e. the two amino acids are linked by a peptide bond) amino acid. The term "peptide" as used herein encompasses amino acid sequences in which carboxyl and/or amino groups are protected or unprotected. Suitable protecting groups for the carboxyl groups of the amino acids include OtBu, OBzl, or OFm. Suitable protecting groups for the amino groups of the amino acids include Fmoc, Boc, Mmt, Mtt, Cbz, or Trt.

The term, "fragment" as used herein refers to a sequence of two or more amino acids present in plecanatide. The amino acids in the fragment may be protected or unprotected.

The term "protected peptide" or "protected peptide fragment" refers to a peptide or peptide fragment, in which all reactive groups of amino acids are masked by protecting groups, unless otherwise specified. Suitable protecting groups for the N-terminal amino acid include 9-fluorenylmethyloxycarbonyl (Fmoc), tert-butoxycarbonyl (Boc), benzoyl (Bz), acetyl (Ac), and benzyl (Bn). Preferably the N-terminal protecting group is Fmoc or Boc, and more preferably Fmoc. Suitable protecting groups for C-terminal amino acid include trityl (triphenylmethyl, Trt) and O-tert-butyl (OtBu). Examples of protecting groups for thiol include acetamidomethyl (Acm), tert-butyl (tBu), 3-nitro-2-pyridinesulfenyl (NPYS), 2-pyridinesulfenyl (Pyr), and trityl (Trt).

Embodiments of the present disclosure relate to an improved process for the preparation of plecanatide.

The present invention relates to an improved process for obtaining plecanatide by means of solid phase synthesis using Wang resin and 2-chlorotrityl chloride (2-ClTrt) resin. The process of the present invention involves coupling of appropriate protected amino acids in a required sequence, cleavage and deprotection, followed by oxidation and purification to get plecanatide.

Inventors of the present invention have developed an improved process which is a simple, efficient and cost-effective process and provides the desired compounds in improved yield and purity and that addresses the problems associated with the processes reported in the prior art. The process of the present invention does not involve use of any toxic and/or costly solvents, also does not involve use of costlier coupling agents and reagents. Accordingly, the present invention provides a process for the preparation of plecanatide, which is simple, efficient, cost effective, high pure and commercially scalable for large scale operations.

In an embodiment, the process for preparing plecanatide of the present invention relates to 5+11 fragments coupling strategy. In particular, the process for preparing plecanatide of the present invention involves coupling fragment A with fragment B to obtain plecanatide. The fragment A is synthesized using 2-chlorotrityl chloride (2-ClTrt) resin and the fragment B is synthesized using Wang resin. The isolated and fully protected fragment A is coupled with Wang resin bound fragment B to obtain a Wang resin bound fully protected peptidyl fragment.

In an embodiment of the present invention, the Wang resin bound fully protected peptidyl fragment is cleaved and globally deprotected using a cleavage cocktail mixture, trifluoroacetic acid/triisopropylsilane/DODT/water (TFA/TIS/DODT/water) to obtain a linear fully deprotected peptide chain.

In an embodiment, fragment A of the present invention consist of five amino acid units length. Fragment A is selected from the peptide, Fmoc-Asn(Trt)-Asp(OtBu)-Glu(OtBu)-Cys(Trt)-Glu(OtBu)-OH (SEQ ID NO: 3) or Boc-Asn(Trt)-Asp(OtBu)-Glu(OtBu)-Cus(Trt)-Glu(OtBu)-OH (SEQ ID NO: 4). Further, fragment A is represented as Fmoc-AA1-AA5-OH or Boc-AA1-AA5-OH.

In an embodiment, fragment B (SEQ ID NO:5) of the present invention consist of 11 amino acid unit length bound with Wang resin. Wang resin bound fragment B is represented as H₂N-Leu-Cys(Acm)-Val-Asn(Trt)-Val-Ala-Cys(Trt)-Thr (OtBu)-Gly-Cys(Acm)-Leu-O-Wang resin (SEQ ID NO: 5). Fragment B is also represented as H₂N-AA6-AA16-O-Wang resin.

In an embodiment, the scheme 1 of the present invention is shown in FIG. 1, which demonstrates the schematic description of the general strategy for process of preparation of plecanatide. The process for preparation of plecanatide as shown in scheme-1 includes the steps of solid phase synthesis of fragment A and fragment B, coupling of peptide fragments, cleaving and deprotecting the resin bound peptide fragments, monocyclizing, dicyclizing and finally desalting the dicyclic peptide to obtain the pure plecanatide.

In an embodiment, the process for the preparation of plecanatide comprising the following steps:
(a) coupling fragment A (SEQ ID NO:3) or (SEQ ID NO:4) with Wang resin bound fragment B (SEQ ID NO:5) to obtain a Wang resin bound protected peptide fragment;
(b) cleaving and deprotecting the Wang resin bound protected peptide fragment obtained in step (a) using reagents, trifluoroacetic acid/triisopropylsilane/DODT/water to obtain a linear chain of formula (I), H₂N-Asn1-Asp2-Glu3-Cys4-Glu5-Leu6-Cys(Acm)7-Val8-Asn9-Val10-Ala11-Cys12-Thr13-Gly 14-Cys(Acm) 15-Leu16-OH (SEQ ID NO: 8);
(c) monocylizing the linear chain of formula (I), H₂N-Asn1-Asp2-Glu3-Cys4-Glu5-Leu6-Cys(Acm)7-Val8-Asn9-Val10-Ala11-Cys12-Thr13-Glyl4-Cys(Acm)15-Leu16-OH (SEQ ID NO: 8) with a suitable reagent to obtain a monocyclic peptide of formula (VI) (SEQ ID NO: 9), (SEQ ID NO: 9)

Asn-Asp-Glu-Cys-Glu-Leu-Cys(Acm)-Val-Asn-Val-Ala-Cys-Thr-Gly-Cys(Acm)-Leu-OH ;

(d) purifying the monocyclic peptide of formula (VI) (SEQ ID NO: 9) obtained in step (a) using reverse phase column chromatography;
(e) dicyclising the monocyclic peptide of formula (VI) (SEQ ID NO: 9) obtained in step (b) with suitable reagents to obtain plecanatide of formula (VII) (SEQ ID NO: 1), (SEQ ID NO: 1)

Asn-Asp-Glu-Cys-Glu-Leu-Cys-Val-Asn-Val-Ala-Cys-Thr-Gly-Cys-Leu-OH ;

and
(f) purifying and desalting the dicyclic peptide of formula (VII) (SEQ ID NO: 1) obtained in step (e) using reverse phase column chromatography to obtain pure plecanatide (SEQ ID NO: 1).

The process of the present invention includes solid phase syntheses of suitable peptide fragments, subsequent fragment condensation in a solution to form a linear crude peptide, and optional oxidative cyclization of cysteine amino acid residues of the linear crude peptide to form the cyclized final product.

The fragments A (SEQ ID NO:3) or (SEQ ID NO:4) and B (SEQ ID NO:5) of the present invention are prepared by solid phase synthesis using the 2-chlorotrityl chloride (2-Cl-Trt) resin and Wang resin respectively. The fragments described above can be prepared by standard solid phase peptide synthesis techniques in which a peptide linkage occurs through the direct condensation of the amino group (i.e., NH₂) of a first amino acid with the carboxy group (i.e., COOH) of a second amino acid with the elimination of a water molecule.

In an embodiment, the Wang resin is bound with amino acid at the temperature in the range of 25° C. to 65° C. under stirring for 2 to 9 hours. Preferably the temperature is in the range of 25-30° C. under stirring for 7 to 9 hours or 45-65° C. under stirring for 2 to 4 hours. More preferably, the temperature is in the range of 45° C. to 50° C. under stirring for 3 hours.

In an embodiment, the Wang resin bound fragment B, H₂N-Leu-Cys(Acm)-Val-Asn(Trt)-Val-Ala-Cys(Trt)-Thr (OtBu)-Gly-Cys(Acm)-Leu-O-Wang (SEQ ID NO: 5) resin of the present invention is prepared by coupling amino acids at the temperature in the range of 25° C. to 65° C. under stirring for 20 minutes to 4 hours. Preferably the temperature is in the range of 25-30° C. under stirring for 2 to 4 hours or 45-65° C. under stirring for 20 to 30 minutes. More preferably, the temperature is in the range of 45° C. to 50° C. under stirring for 20 minutes.

In an embodiment, the coupling of fragment A and B of the present invention involves using coupling reagent combinations. Example of suitable coupling reagent combinations includes, but not limited to, N,N'-diisopropylcarbodiimide-1-hydroxybenzotriazole (DIC-HOBt), hexafluorophosphate benzotriazole tetramethyl uronium-hexafluorophosphate azabenzotriazole tetramethyl uranium (HBTU-HATU), hexafluorophosphate benzotriazole tetramethyl uronium-1-hydroxybenzotriazole (HBTU-HOBt), tetrafluoroboratebenzotriazole tetramethyluronium-1-hydroxybenzotriazole (TBTU-HOBt). Preferably, the coupling reagent combination is N,N'-diisopropylcarbodiimide and 1-hydroxybenzotriazole (DIC-HOBt).

In an embodiment, the fragment A and Wang resin bound fragment B of the present invention is coupled at the temperature in the range of 25° C. to 65° C. under stirring for 45 minutes to 5 hours. Preferably the temperature is in the range of 25-30° C. under stirring for 3 to 5 hours or 45-65° C. under stirring for 45 minutes to 1 hour. More preferably, the temperature is in the range of 45° C. to 50° C. under stirring for 45 minutes.

In an embodiment, the concentration of reaction mass in the mono cyclization of linear peptide of formula (I) is in the range of 0.5-1.0 mg/mL. Preferably, the concentration of the reaction mass is 1.0 mg/mL.

While the foregoing describes various embodiments of the disclosure, other and further embodiments of the disclosure may be devised without departing from the basic scope thereof. The scope of the invention is determined by the claims that follow. The invention is not limited to the described embodiments, versions or examples, which are included to enable a person having ordinary skill in the art to make and use the invention when combined with information and knowledge available to the person having ordinary skill in the art.

For the purpose of clarity and as an aid in the understanding of the invention, as disclosed and claimed herein, the following terms and abbreviations are defined below:

Boc: t-Butyloxycarbonyl
Cbz: Benzyloxycarbonyl
DCM: Dichloromethane
DIC: N,N'-Diisopropylcarbodiimide
DIPEA: Diisopropylethylamine
DMF: Dimethylformamide
EDT: Ethanedithiol
Fmoc: 9-Fluorenylmethoxycarbonyl
HATU: Hexafluorophosphate azabenzotriazole tetramethyluronium
HBTU: Hexafluorophosphate benzotriazole tetramethyluronium
HOAt: Hydroxy-7-azabenzotriazole
HOBt: N-Hydroxybenzotriazole
HPLC: High Performance Liquid Chromatography
MTBE: Methyl-t-butyl ether
OBt: O-Benzotriazole
OBzl: O-Benzyl
OtBu: tert-Butyl ester
TBTU: Tetrafluoroboratebenzotriazole tetramethyluronium
tBu: tert-Butyl
TFA: Trifluoroacetic acid
Trt: Trityl

EXAMPLES

The present invention is further explained in the form of following examples. However, it is to be understood that the following examples are merely illustrative and are not to be taken as limitations upon the scope of the invention.

Example 1: Synthesis of Fragment A, Fmoc-AA1-AA5-OH

Synthesis of H$_2$N-Glu(OtBu)-O-2-ClTrt: 2-ClTrt resin (50 g, substitution=1.0 mmol/g resin) was charged into a peptide synthesis flask and washed twice with dichloromethane (500 mL). The resin was suspended in dichloromethane (DCM) (500 mL) without stirring for 30 min. The resin was added with a clear mixture of Fmoc-Glu(OtBu)-OH (2.0 equiv), DIPEA (3.0 equiv) and DMF (500 mL). The suspension was gently agitated under nitrogen bubbling and mild stirring at 25-30° C. for 2 h. The reaction mass was then drained and resin was washed with DMF (3×500 mL) and DCM (3×500 mL). The resin obtained was added with a mixture of 10% DIPEA in methanol and the suspension was stirred for 30 min and drained the solvent. The resin obtained was washed with DMF (3×500 mL) and DCM (3×500 mL).

The resin obtained above was added with a clear mixture of 20% piperidine in DMF (500 mL). The suspension was gently agitated under nitrogen bubbling and mild stirring at 25-30° C. for 10 minutes and drained the solvent. The resin obtained was further added with a clear mixture of 20% piperidine in DMF (500 mL) and the suspension was stirred at 25-30° C. for 10 min, drained the solvent and the resin was washed with DMF (3×500 mL), IPA (500 mL) and DCM (3×500 mL) to obtain H$_2$N-Glu(OtBu)-O-2-ClTrt. Completion of the Fmoc-deprotection was confirmed by Kaiser colour test.

Synthesis of Fmoc-Asn(Trt)-Asp(OtBu)-Glu(OtBu)-Cys(Trt)-Glu(OtBu)-O-2-ClTrt (SEQ ID NO: 2): A clear mixture of Fmoc-Cys(Trt)-OH (2.0 equiv), N,N-diisopropylcarbodiimide (DIC) (2.0 equiv) and 1-Hydroxybenzotriazole (HOBt) (2.0 equiv) in DMF (500 mL) was added to the H$_2$N-Glu(OtBu)-O-2-ClTrt. The suspension was gently agitated under nitrogen bubbling and mild stirring at 25-30° C. for 3 h. Completion of the reaction was monitored by Kaiser colour test. After completion of the reaction, drained solvent and the resin was washed with DMF (3×500 mL) and DCM (3×500 mL). The same process of coupling and Fmoc-deprotection was followed for Fmoc-Glu(OtBu)-OH, Fmoc-Asp (OtBu)-OH and Fmoc-Asn(Trt)-OH or Boc-Asn(Trt)-OH to get a 2-ClTrt resin bound peptide chain of formula, Fmoc-Asn(Trt)-Asp(OtBu)-Glu(OtBu)-Cys(Trt)-Glu(OtBu)-O-2-ClTrt resin (SEQ ID NO: 2).

Synthesis of Fmoc-Asn(Trt)-Asp(OtBu)-Glu(OtBu)-Cys(Trt)-Glu(OtBu)-OH: 2-ClTrt resin (SEQ ID NO: 2) bound fragment obtained in above step was charged into a peptide synthesis flask. The resin was suspended in dichloromethane (DCM) (500 mL) without stirring for 10 min and added 1.0% TFA in DCM (4×250 mL). The suspension was gently agitated under nitrogen bubbling and mild stirring at 25-30° C. for 10 min each and drained the solvent into a round bottomed flask. The collected solution containing Fragment A was washed twice (2×1000 mL) with water and the organic layer evaporated. The thick syrupy mass obtained after evaporation was dissolved in MTBE (25 mL) and precipitated by addition of n-hexane (150 mL) to obtain an off-white precipitate of Fragment A (SEQ ID NO: 3), Fmoc-AA1-AA5-OH. The precipitated solid was filtered through Buckner funnel and washed with n-hexane (2×150 mL). The solid was then dried in a vacuum oven under high vacuum at 35-40° C. till constant weight. Yield: 90%, Purity by HPLC: 95%.

Example 2: Synthesis of Fragment B, H$_2$N-Leu-Cys(Acm)-Val-Asn(Trt)-Val-Ala-Cys(Trt)-Thr(OtBu)-Gly-Cys(Acm)-Leu-O-Wang Resin (SEQ ID NO: 5)

Synthesis of H$_2$N-Leu-O-Wang resin: Wang resin (15 g, substitution=0.5 mmol/g resin) was charged into a peptide synthesis flask and washed twice with dichloromethane (500 mL). The resin was suspended in dichloromethane (DCM) (500 mL) without stirring for 30 min. A clear mixture of Fmoc-Leu-OH (3.0 equiv, 8.0 g), N,N-diisopropylcarbodiimide (3.0 equiv, 3.5 mL) and 1-hydroxybenzotriazole (3.0 equiv, 3.5 g) and DMAP (0.1 equiv, 0.09 g) in DMF (75 mL) were added. The suspension was gently agitated under nitrogen bubbling and mild stirring at 45-50° C. for 3 h. After completion of the reaction, the solvent was drained and the resin was washed with DMF (3×150 mL) and DCM (3×150 mL). The resin obtained was added with a mixture of acetic anhydride:pyridine:DCM (0.1:0.2:9.7 with respect to weight of resin). The suspension was stirred for 30 min and drained the solvent. The resin was washed with DMF (3×150 mL) and DCM (3×150 mL).

The resin obtained in the above step was added with a clear mixture of 20% piperidine in DMF (150 mL). The suspension was gently agitated under nitrogen bubbling and mild stirring at 25-30° C. for 10 min, drained the solvent and the resin was further added with a clear mixture of 20% piperidine in DMF (150 mL). The suspension was stirred at 25-30° C. for 10 min, drained the solvent and washed the resin with DMF (3×150 mL), IPA (150 mL) and DCM (3×150 mL) to obtain H₂N-Leu-O-Wang resin. Completion of the Fmoc-deprotection was confirmed by Kaiser colour test.

Synthesis of H₂N-Cys(Acm)-Leu-O-Wang resin: A clear mixture of Fmoc-Cys(Acm)-OH (2.0 equiv), N,N-diisopropylcarbodiimide (DIC) (2.0 equiv) and 1-hydroxybenzotriazole (HOBt) (2.0 equiv) in DMF (500 mL) was added to the resin. The suspension was gently agitated under nitrogen bubbling and mild stirring at 45-50° C. for 20 minutes. Progress of the reaction was monitored by Kaiser colour test. After completion of the reaction, the solvent was drained and washed the resin with DMF (3×150 mL) and DCM (3×150 mL) to obtain H₂N-Cys(Acm)-Leu-O-Wang resin.

The same process of coupling and deprotection was followed for Fmoc-Gly-OH, Fmoc-Thr (OtBu)-OH, Fmoc-Cys(Trt)-OH, Fmoc-Ala-OH, Fmoc-Val-OH, Fmoc-Asn(Trt)-OH, Fmoc-Val-OH, Fmoc-Cys(Acm)-OH, and Fmoc-Leu-OH to obtain fragment B, H₂N-AA6-AA16-O-Wang resin (SEQ ID NO: 5).

Example 3: Coupling of Fragment A and Fragment B

A clear mixture of Fmoc-Asn(Trt)-Asp(OtBu)-Glu(OtBu)-Cys(Trt)-Glu(OtBu)-OH (Fragment A) (SEQ ID NO: 3) (2.0 equiv, 22.2 g), N, N-diisopropylcarbodiimide (3.0 equiv, 3.5 mL) and 1-hydroxybenzotriazole (3.0 equiv, 3.5 g) in DMF (150 mL) was added to the resin. The suspension was gently agitated under nitrogen bubbling and mild stirring at 45-50° C. for 45 minutes. Progress of the reaction was monitored by Kaiser colour test. After completion of the reaction, drained the solvent and washed the resin with DMF (3×150 mL) and DCM (3×150 mL) to obtain Fmoc-Asn(Trt)-Asp(OtBu)-Glu(OtBu)-Cys(Trt)-Glu(OtBu)-Leu-Cys(Acm)-Val-Asn(Trt)-Val-Ala-Cys(Trt)-Thr(OtBu)-Gly-Cys(Acm)-Leu-O-Wang resin (SEQ ID NO: 6). The resin obtained was treated with a clear mixture of 20% piperidine in DMF (150 mL). The suspension was gently agitated under nitrogen bubbling and mild stirring at 25-30° C. for 10 min, drained the solvent and the resin was further added with a clear mixture of 20% piperidine in DMF (150 mL). The suspension was stirred at 25-30° C. for 10 min, drained the solvent and washed the resin with DMF (3×150 mL), DCM (3×150 mL), IPA (150 mL), MTBE (3×150 mL) to obtain H₂N-Asn(Trt)-Asp(OtBu)-Glu(OtBu)-Cys(Trt)-Glu(OtBu)-Leu-Cys(Acm)-Val-Asn(Trt)-Val-Ala-Cys(Trt)-Thr(OtBu)-Gly-Cys(Acm)-Leu-O-Wang resin (SEQ ID NO: 7). Completion of the Fmoc-deprotection was confirmed by Kaiser colour test.

Example 4: Synthesis of Formula (I), H₂N-Asn-Asp-Glu-Cys-Glu-Leu-Cys(Acm)-Val-Asn-Val-Ala-Cys-Thr-Gly-Cys(Acm)-Leu-OH (SEQ ID NO: 7)

H₂N-Asn(Trt)-Asp(OtBu)-Glu(OtBu)-Cys(Trt)-Glu(OtBu)-Leu-Cys(Acm)-Val-Asn(Trt)-Val-Ala-Cys(Trt)-Thr(OtBu)-Gly-Cys(Acm)-Leu-O-Wang resin (SEQ ID NO: 7) was added to pre-cooled mixture of TFA:TIPS:DODT:Water (9:0.5:0.25:0.25 vol, 220 mL) at 0-10° C. The suspension was gently stirred at 25-30° C. for 3 hours. The resin was filtered through a sintered funnel. The filtrate was added into pre-cooled methyl tertiary-butyl ether (1100 mL) at 0-10° C. The reaction mixture was stirred at 0-10° C. for 30 min and at 25-30° C. for 1 h. The precipitated solid obtained was then filtered and washed with MTBE (3×250 mL). The suction dried solid was then dried in a vacuum oven at 35-40° C. till constant weight to obtain dried H₂N-Asn-Asp-Glu-Cys-Glu-Leu-Cys(Acm)-Val-Asn-Val-Ala-Cys-Thr-Gly-Cys(Acm)-Leu-OH (SEQ ID NO: 8). Yield: 80%, Purity by HPLC: 50%.

Example 5: Synthesis of Monocyclic Peptide of Formula (VI)

The linear peptide of the formula (I) (SEQ ID NO: 8) obtained in example 4 was added in water maintaining the concentration of the reaction mass to 1 mg/mL. The pH of the reaction mass was adjusted to 8.5-9.5 using ammonium hydroxide. The reaction mass was added with 1% H₂O₂ solution. The reaction mass was stirred for 2 hours at 25-30° C. The progress of the reaction was monitored by HPLC. After completion of the reaction, pH of the reaction mass was adjusted to 5.5-6.5 using acetic acid or TFA. The reaction mass was filtered through 1.2µ filter paper. The filtrate obtained is subjected to reverse phase column chromatography for purification. Purity of reaction mass by HPLC: 55%.

The crude monocyclic peptide of formula (VI) (SEQ ID NO: 9) obtained above is loaded to a column without further dilution. The details of the reverse phase column chromatography are as follows.
Column specification: 250×80 mm
Media Specification: C-18, 10µ, 100-120A°
Mobile Phase A: 0.02M Triethyl ammonium phosphate in water of pH 6.5. Mobile Phase B: Acetonitrile.

The monocyclic peptide of formula (VI) (SEQ ID NO: 9) was obtained from the fractions having HPLC purity ≥75%. Fractions having HPLC purity ≤75% and ≥45% were pooled for re-purification using the same method.

Example 6: Synthesis of Plecanatide

The monocylic peptide (SEQ ID NO: 9) obtained in the Example-5 was diluted with water for maintaining the concentration of the reaction mass to about 0.5 mg/mL. The pH of the reaction mass was adjusted to 1-2 using 10% aqueous trifluoroacetic acid. The reaction mass was added with iodine (2 equiv) as a methanolic solution till the yellow colour of the reaction mass persists for more than 10 min. The reaction mass was stirred for 2 hours at 25-30° C. The progress of the reaction was monitored by HPLC. After completion of the reaction, the excess iodine is quenched with ascorbic acid and pH of the reaction mass was adjusted to 5.5-6.5 using ammonium hydroxide. The reaction mass was filtered through 1-1.2 u filter paper to obtain crude dicyclized peptide (SEQ ID NO: 1) as filtrate. Purity of reaction mass by HPLC: 65%.

The crude dicyclic peptide (SEQ ID NO: 1) obtained above was subjected to reverse phase column chromatography for purification. The filtrate containing crude dicyclic peptide was loaded to the column after diluting with water to maintain the concentration of acetonitrile to ≤2%. The details of the reverse phase column chromatography are as follows.

Column specification: 250×80 mm
Media Specification: C-18, 10µ, 100-120 A°
Mobile Phase A: 0.02M Triethyl ammonium phosphate in water of pH 6.5 or 0.1% TFA in water, Mobile Phase B: Acetonitrile.

The dicyclic peptide (SEQ ID NO: 1) was obtained from the fractions having HPLC purity ≥94% and single maximum impurity ≤3%. The dicyclic peptide (SEQ ID NO: 1) obtained was pooled for desalting. The fractions having HPLC purity ≤94% and ≥80% were pooled for re-purification using same method.

Desalting: The dicyclic peptide (SEQ ID NO: 1) obtained above was diluted with equal amount of water. The solution was loaded to reverse phase column chromatography for desalting. The details of the reverse phase column chromatography are as follows.

Media Specification: C-18, 10µ, 100-120 A°
Mobile Phase A: 0.05% ammonium hydroxide, Mobile Phase B: Acetonitrile, Mobile Phase C: 0.25M ammonium acetate in water, Mobile Phase D: 0.02M Triethyl ammonium phosphate in water of pH 6.5 or 0.1% TFA in water The plecanatide (SEQ ID NO: 1) was obtained from the fractions having HPLC purity ≥97.5% and single maximum impurity ≤1%. The fractions having HPLC purity ≤97.5% and ≥85% were pooled for re-purification using the same method as described above.

Lyophilization: The pooled fractions obtained from desalting were filtered through 0.2µ filter and subjected to lyophilization to obtain dry plecanatide (SEQ ID NO: 1).

The foregoing examples are merely illustrative and are not to be taken as limitations upon the scope of the invention. Various changes and modifications to the disclosed embodiments will be apparent to those skilled in the art. Such changes and modifications may be made without departing from the scope of the invention.

The present invention provides an improved process of preparing plecanatide which is a simple, efficient and cost-effective process.

The present invention provides an improved process of preparing plecanatide which gives higher yield and purity.

The present invention provides an improved process of preparing plecanatide which furnishes intermediates and crude plecanatide which has minimum or no deletion impurities. This gives advantage in ease of purification and yield of the final isolated plecanatide.

The present invention provides an improved process of preparing plecanatide by employing a 11+5 strategy which results into better peptide content in the crude material which otherwise is a challenge if sequential coupling strategy is followed.

The present invention provides an improved process of preparing plecanatide which gives a purified monocyclic intermediate which is of high purity and peptide content resulting into better yields during dicyclization followed by purification.

The present invention provides process of preparing fragment B in which coupling time for each amino acid is less than 30 min when coupling reaction is performed at 45° C. This not only reduces the reaction time but also ensures complete coupling of all the amino acids in the sequence.

We claim:

1. A process for preparing plecanatide comprising the steps of:

(a) coupling a fragment A, wherein fragment A is selected from the group consisting of: Fmoc-Asn(Trt)-Asp(OtBu)-Glu(OtBu)-Cys(Trt)-Glu(OtBu)-OH (SEQ ID NO: 3) and Boc-Asn(Trt)-Asp(OtBu)-Glu(OtBu)-Cys(Trt)-Glu(OtBu)-OH (SEQ ID NO: 4), with Wang resin bound fragment B: H$_2$N-Leu-Cys(Acm)-Val-Asn(Trt)-Val-Ala-Cys(Trt)-Thr(OtBu)-Gly-Cys(Acm)-Leu-O-Wang resin (SEQ ID NO:5) using a coupling reagent to obtain a Wang resin bound protected peptide fragment: Fmoc-Asn(Trt)-Asp(OtBu)-Glu(OtBu)-Cys(Trt)-Glu(OtBu)-Leu-Cys(Acm)-Val-Asn(Trt)-Val-Ala-Cys(Trt)-Thr(OtBu)-Gly-Cys(Acm)-Leu-O-Wang resin (SEQ ID NO:6);

(b) cleaving and deprotecting the Wang resin bound protected peptide fragment obtained in a step (a) using a mixture of trifluoroacetic acid/triisopropylsilane/DODT/Water to obtain a linear chain of formula (I); H$_2$N-Asn1-Asp2-Glu3-Cys4-Glu5-Leu6-Cys(Acm)7-Val8-Asn9-Val10-Ala11-Cys12-Thr13-Gly14-Cys(Acm)15-Leu16-OH (SEQ ID NO:8);

(c) monocyclizing the linear chain of formula (I), H$_2$N-Asn1-Asp2-Glu3-Cys4-Glu5-Leu6-Cys(Acm)7-Val8-Asn9-Val10-Ala11-Cys12-Thr13-Gly14-Cys(Acm)15-

Leu16-OH (SEQ ID NO:8) with 1% $H_2O_2$ to obtain a monocyclic peptide of formula (VI):

(SEQ ID NO: 9)

Asn-Asp-Glu-Cys-Glu-Leu-Cys(Acm)-Val-Asn-Val-Ala-Cys-Thr-;
Gly-Cys(Acm)-Leu-OH (with a bond connecting the two Cys residues without Acm)

(d) purifying the monocyclic peptide of formula (VI) (SEQ ID NO:9) obtained in step (c) using reverse phase column chromatography, (e) dicyclizing the monocyclic peptide of formula (VI) (SEQ ID NO:9) obtained in step (d) with 2% iodine to obtain a dicyclic peptide of formula (VII):

(SEQ ID NO: 1)

Asn-Asp-Glu-Cys-Glu-Leu-Cys-Val-Asn-Val-Ala-Cys-Thr-Gly-Cys-Leu-;
OH and (f) purifying and desalting the dicyclic peptide of formula (VII) (SEQ ID NO:1) obtained in step (e) using reverse phase column chromatography to obtain pure plecanatide.

2. The process for preparing plecanatide as claimed in claim 1, wherein the reverse phase column chromatography for purifying the monocyclic peptide of formula (VI) has column specification: 250×80 mm, media specification: C-18, 10μ, 100 A°, mobile phase A: 0.02M triethyl ammonium phosphate in water of pH 6.5 and mobile phase B: acetonitrile.

3. The process for preparing plecanatide as claimed in claim 1, wherein the reverse phase column chromatography for purifying the dicyclic peptide of formula (VII) has column specification: 250×80 mm, media specification: C-18, 7-10μ, 100 A°, mobile phase A: 0.02 M triethyl ammonium phosphate in water of pH 6.5 and mobile phase B: acetonitrile.

4. The process for preparing plecanatide as claimed in claim 1, wherein the reverse phase column chromatography for desalting the dicyclic peptide of formula (VII) has column specification: 250×80 mm, media specification: C-18, 10μ, 100 A°, mobile phase A: 0.025% ammonium hydroxide, mobile phase B: acetonitrile, mobile phase C: 0.1-0.2M ammonium acetate in water and mobile phase D: 0.1% trifluoroacetic acid in water.

5. The process for preparing plecanatide as claimed in claim 1, wherein the reverse phase column chromatography for purifying the dicyclic peptide of formula (VII) has column specification: 250×80 mm, media specification: C-18, 10μ, 100 A°, mobile phase A: 0.1-0.2% trifluoroacetic acid in water and mobile phase B: acetonitrile.

6. The process for preparing plecanatide as claimed in claim 1, wherein the fragment A and fragment B are prepared using solid-phase peptide synthesis.

7. The process for preparing plecanatide as claimed in claim 1, wherein the mixture of trifluoroacetic acid/triisopropylsilane/3,6-dioxa-1,8-octanedithiol/water is in the ratio of 9:0.5:0.25:0.25 v/v respectively.

8. The process for preparing plecanatide as claimed in claim 1 wherein the Wang resin bound fragment B is prepared by coupling amino acids at a temperature in the range of 25° C. to 65° C. under stirring for 20 minutes to 3 hours.

9. The process for preparing plecanatide as claimed in claim 1, wherein the fragment A and the Wang resin bound fragment B in step (a) are coupled at a temperature in the range of 25° C. to 65° C. under stirring for 45 minutes to 5 hours.

* * * * *

SEQUENCE LISTING

```
<160> NUMBER OF SEQ ID NOS: 9

<210> SEQ ID NO 1
<211> LENGTH: 16
<212> TYPE: PRT
<213> ORGANISM: Artificial Sequence
<220> FEATURE:
<223> OTHER INFORMATION: Plecanatide
<220> FEATURE:
<221> NAME/KEY: DISULFID
<222> LOCATION: (4)..(12)
<220> FEATURE:
<221> NAME/KEY: DISULFID
<222> LOCATION: (7)..(15)

<400> SEQUENCE: 1

Asn Asp Glu Cys Glu Leu Cys Val Asn Val Ala Cys Thr Gly Cys Leu
1               5                   10                  15

<210> SEQ ID NO 2
<211> LENGTH: 5
<212> TYPE: PRT
<213> ORGANISM: Artificial Sequence
<220> FEATURE:
<223> OTHER INFORMATION: ClTrt resin bound peptide (Fmoc protected)
<220> FEATURE:
<221> NAME/KEY: MISC_FEATURE
<222> LOCATION: (1)..(1)
<223> OTHER INFORMATION: 9-fIuorenylmethyloxycarbonyl
<220> FEATURE:
```

```
<221> NAME/KEY: MISC_FEATURE
<222> LOCATION: (1)..(1)
<223> OTHER INFORMATION: trity
<220> FEATURE:
<221> NAME/KEY: MISC_FEATURE
<222> LOCATION: (2)..(2)
<223> OTHER INFORMATION: tert-butyl
<220> FEATURE:
<221> NAME/KEY: MISC_FEATURE
<222> LOCATION: (3)..(3)
<223> OTHER INFORMATION: tert-butyl
<220> FEATURE:
<221> NAME/KEY: MISC_FEATURE
<222> LOCATION: (4)..(4)
<223> OTHER INFORMATION: trityl
<220> FEATURE:
<221> NAME/KEY: MISC_FEATURE
<222> LOCATION: (5)..(5)
<223> OTHER INFORMATION: 2-chlorotrityl chloride (2-ClTrt) resin

<400> SEQUENCE: 2

Asn Asp Glu Cys Glu
1               5

<210> SEQ ID NO 3
<211> LENGTH: 5
<212> TYPE: PRT
<213> ORGANISM: Artificial Sequence
<220> FEATURE:
<223> OTHER INFORMATION: Fragment A (Fmoc protected)
<220> FEATURE:
<221> NAME/KEY: MISC_FEATURE
<222> LOCATION: (1)..(1)
<223> OTHER INFORMATION: 9-fIuorenylmethyloxycarbonyl
<220> FEATURE:
<221> NAME/KEY: MISC_FEATURE
<222> LOCATION: (1)..(1)
<223> OTHER INFORMATION: trityl
<220> FEATURE:
<221> NAME/KEY: MISC_FEATURE
<222> LOCATION: (2)..(2)
<223> OTHER INFORMATION: tert-butyl
<220> FEATURE:
<221> NAME/KEY: MISC_FEATURE
<222> LOCATION: (3)..(3)
<223> OTHER INFORMATION: tert-butyl
<220> FEATURE:
<221> NAME/KEY: MISC_FEATURE
<222> LOCATION: (4)..(4)
<223> OTHER INFORMATION: trityl
<220> FEATURE:
<221> NAME/KEY: MISC_FEATURE
<222> LOCATION: (5)..(5)
<223> OTHER INFORMATION: tert-butyl

<400> SEQUENCE: 3

Asn Asp Glu Cys Glu
1               5

<210> SEQ ID NO 4
<211> LENGTH: 5
<212> TYPE: PRT
<213> ORGANISM: Artificial Sequence
<220> FEATURE:
<223> OTHER INFORMATION: Fragment A (Boc protected)
<220> FEATURE:
<221> NAME/KEY: MISC_FEATURE
<222> LOCATION: (1)..(1)
<223> OTHER INFORMATION: 1 - tert-butoxycarbonyl
<220> FEATURE:
<221> NAME/KEY: MISC_FEATURE
<222> LOCATION: (1)..(1)
<223> OTHER INFORMATION: trityl
<220> FEATURE:
<221> NAME/KEY: MISC_FEATURE
```

```
<222> LOCATION: (2)..(2)
<223> OTHER INFORMATION: tert-butyl
<220> FEATURE:
<221> NAME/KEY: MISC_FEATURE
<222> LOCATION: (3)..(3)
<223> OTHER INFORMATION: tert-butyl
<220> FEATURE:
<221> NAME/KEY: MISC_FEATURE
<222> LOCATION: (4)..(4)
<223> OTHER INFORMATION: trityl
<220> FEATURE:
<221> NAME/KEY: MISC_FEATURE
<222> LOCATION: (5)..(5)
<223> OTHER INFORMATION: tert-butyl

<400> SEQUENCE: 4

Asn Asp Glu Cys Glu
1               5

<210> SEQ ID NO 5
<211> LENGTH: 11
<212> TYPE: PRT
<213> ORGANISM: Artificial Sequence
<220> FEATURE:
<223> OTHER INFORMATION: Fragment B
<220> FEATURE:
<221> NAME/KEY: MISC_FEATURE
<222> LOCATION: (2)..(2)
<223> OTHER INFORMATION: acetamidomethyl
<220> FEATURE:
<221> NAME/KEY: MISC_FEATURE
<222> LOCATION: (4)..(4)
<223> OTHER INFORMATION: trityl
<220> FEATURE:
<221> NAME/KEY: MISC_FEATURE
<222> LOCATION: (7)..(7)
<223> OTHER INFORMATION: trityl
<220> FEATURE:
<221> NAME/KEY: MISC_FEATURE
<222> LOCATION: (8)..(8)
<223> OTHER INFORMATION: tert-butyl
<220> FEATURE:
<221> NAME/KEY: MISC_FEATURE
<222> LOCATION: (9)..(9)
<223> OTHER INFORMATION: acetamidomethyl
<220> FEATURE:
<221> NAME/KEY: MISC_FEATURE
<222> LOCATION: (11)..(11)
<223> OTHER INFORMATION: Wang resin

<400> SEQUENCE: 5

Leu Cys Val Asn Val Ala Cys Thr Gly Cys Leu
1               5                   10

<210> SEQ ID NO 6
<211> LENGTH: 16
<212> TYPE: PRT
<213> ORGANISM: Artificial Sequence
<220> FEATURE:
<223> OTHER INFORMATION: Wang resin bound protected peptide fragment
<220> FEATURE:
<221> NAME/KEY: MISC_FEATURE
<222> LOCATION: (1)..(1)
<223> OTHER INFORMATION: 9-fluorenylmethyloxycarbonyl
<220> FEATURE:
<221> NAME/KEY: MISC_FEATURE
<222> LOCATION: (1)..(1)
<223> OTHER INFORMATION: trityl
<220> FEATURE:
<221> NAME/KEY: MISC_FEATURE
<222> LOCATION: (2)..(2)
<223> OTHER INFORMATION: tert-butyl
<220> FEATURE:
<221> NAME/KEY: MISC_FEATURE
<222> LOCATION: (3)..(3)
```

```
<223> OTHER INFORMATION: tert-butyl
<220> FEATURE:
<221> NAME/KEY: MISC_FEATURE
<222> LOCATION: (4)..(4)
<223> OTHER INFORMATION: trityl
<220> FEATURE:
<221> NAME/KEY: MISC_FEATURE
<222> LOCATION: (5)..(5)
<223> OTHER INFORMATION: tert-butyl
<220> FEATURE:
<221> NAME/KEY: MISC_FEATURE
<222> LOCATION: (7)..(7)
<223> OTHER INFORMATION: acetamidomethyl
<220> FEATURE:
<221> NAME/KEY: MISC_FEATURE
<222> LOCATION: (9)..(9)
<223> OTHER INFORMATION: trityl
<220> FEATURE:
<221> NAME/KEY: MISC_FEATURE
<222> LOCATION: (12)..(12)
<223> OTHER INFORMATION: trityl
<220> FEATURE:
<221> NAME/KEY: MISC_FEATURE
<222> LOCATION: (13)..(13)
<223> OTHER INFORMATION: tert-butyl
<220> FEATURE:
<221> NAME/KEY: MISC_FEATURE
<222> LOCATION: (15)..(15)
<223> OTHER INFORMATION: acetamidomethyl
<220> FEATURE:
<221> NAME/KEY: MISC_FEATURE
<222> LOCATION: (16)..(16)
<223> OTHER INFORMATION: Wang resin

<400> SEQUENCE: 6

Asn Asp Glu Cys Glu Leu Cys Val Asn Val Ala Cys Thr Gly Cys Leu
1               5                   10                  15

<210> SEQ ID NO 7
<211> LENGTH: 16
<212> TYPE: PRT
<213> ORGANISM: Artificial Sequence
<220> FEATURE:
<223> OTHER INFORMATION: Wang resin bound dprotected peptide fragment
<220> FEATURE:
<221> NAME/KEY: MISC_FEATURE
<222> LOCATION: (1)..(1)
<223> OTHER INFORMATION: trityl
<220> FEATURE:
<221> NAME/KEY: MISC_FEATURE
<222> LOCATION: (2)..(2)
<223> OTHER INFORMATION: tert-butyl
<220> FEATURE:
<221> NAME/KEY: MISC_FEATURE
<222> LOCATION: (3)..(3)
<223> OTHER INFORMATION: tert-butyl
<220> FEATURE:
<221> NAME/KEY: MISC_FEATURE
<222> LOCATION: (4)..(4)
<223> OTHER INFORMATION: trityl
<220> FEATURE:
<221> NAME/KEY: MISC_FEATURE
<222> LOCATION: (5)..(5)
<223> OTHER INFORMATION: tert-butyl
<220> FEATURE:
<221> NAME/KEY: MISC_FEATURE
<222> LOCATION: (7)..(7)
<223> OTHER INFORMATION: acetamidomethyl
<220> FEATURE:
<221> NAME/KEY: MISC_FEATURE
<222> LOCATION: (9)..(9)
<223> OTHER INFORMATION: trityl
<220> FEATURE:
<221> NAME/KEY: MISC_FEATURE
<222> LOCATION: (12)..(12)
<223> OTHER INFORMATION: trityl
<220> FEATURE:
```

```
<221> NAME/KEY: MISC_FEATURE
<222> LOCATION: (13)..(13)
<223> OTHER INFORMATION: tert-butyl
<220> FEATURE:
<221> NAME/KEY: MISC_FEATURE
<222> LOCATION: (15)..(15)
<223> OTHER INFORMATION: acetamidomethyl
<220> FEATURE:
<221> NAME/KEY: MISC_FEATURE
<222> LOCATION: (16)..(16)
<223> OTHER INFORMATION: Wang resin

<400> SEQUENCE: 7

Asn Asp Glu Cys Glu Leu Cys Val Asn Val Ala Cys Thr Gly Cys Leu
1               5                   10                  15

<210> SEQ ID NO 8
<211> LENGTH: 16
<212> TYPE: PRT
<213> ORGANISM: Artificial Sequence
<220> FEATURE:
<223> OTHER INFORMATION: Formula (I)
<220> FEATURE:
<221> NAME/KEY: MISC_FEATURE
<222> LOCATION: (7)..(7)
<223> OTHER INFORMATION: acetamidomethyl
<220> FEATURE:
<221> NAME/KEY: MISC_FEATURE
<222> LOCATION: (15)..(15)
<223> OTHER INFORMATION: acetamidomethyl

<400> SEQUENCE: 8

Asn Asp Glu Cys Glu Leu Cys Val Asn Val Ala Cys Thr Gly Cys Leu
1               5                   10                  15

<210> SEQ ID NO 9
<211> LENGTH: 16
<212> TYPE: PRT
<213> ORGANISM: Artificial Sequence
<220> FEATURE:
<223> OTHER INFORMATION: Formula (VI)
<220> FEATURE:
<221> NAME/KEY: DISULFID
<222> LOCATION: (4)..(12)
<220> FEATURE:
<221> NAME/KEY: MISC_FEATURE
<222> LOCATION: (7)..(7)
<223> OTHER INFORMATION: acetamidomethyl
<220> FEATURE:
<221> NAME/KEY: MISC_FEATURE
<222> LOCATION: (15)..(15)
<223> OTHER INFORMATION: acetamidomethyl

<400> SEQUENCE: 9

Asn Asp Glu Cys Glu Leu Cys Val Asn Val Ala Cys Thr Gly Cys Leu
1               5                   10                  15
```